United States Patent
Shinoki et al.

(10) Patent No.: US 7,109,314 B2
(45) Date of Patent: Sep. 19, 2006

(54) FLUORESCENT NUCLEOTIDES

(75) Inventors: Hiroshi Shinoki, Saitama (JP); Hiroko Inomata, Saitama (JP); Masayoshi Kojima, Saitama (JP); Yukio Sudo, Saitama (JP); Osamu Seshimoto, Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/829,467

(22) Filed: Apr. 9, 2001

(65) Prior Publication Data

US 2002/0064782 A1 May 30, 2002

(30) Foreign Application Priority Data

Apr. 10, 2000 (JP) .............................. 2000-107675

(51) Int. Cl.
C07H 21/02 (2006.01)
C12Q 1/68 (2006.01)
A61N 57/00 (2006.01)

(52) U.S. Cl. .................. 536/22.1; 536/24.3; 435/6; 514/112; 514/222.2

(58) Field of Classification Search .................. 435/6, 435/7.1, 91.1, 91.2; 536/22.1, 23.1, 24.3–33, 536/25.32; 540/555; 436/546
See application file for complete search history.

(56) References Cited

U.S. PATENT DOCUMENTS

| | | | |
|---|---|---|---|
| 5,486,616 A | 1/1996 | Waggoner et al. | |
| 5,569,587 A | 10/1996 | Waggoner | |
| 5,679,516 A | 10/1997 | Okamoto et al. | ............... 435/6 |
| 5,719,027 A | 2/1998 | Miyazaki et al. | ............... 435/6 |
| 5,719,031 A * | 2/1998 | Haugland et al. | ............ 435/7.4 |
| 5,808,043 A | 9/1998 | Duthie et al. | |
| 5,808,044 A | 9/1998 | Brush et al. | ............. 536/25.32 |
| 5,986,086 A | 11/1999 | Brush et al. | |
| 6,027,709 A | 2/2000 | Little et al. | ................. 424/1.65 |
| 6,130,101 A * | 10/2000 | Mao et al. | ................... 436/546 |
| 6,277,984 B1 * | 8/2001 | Mujunder et al. | ........... 540/555 |
| 6,448,008 B1 * | 9/2002 | Caputo et al. | .................. 435/6 |

FOREIGN PATENT DOCUMENTS

| | | |
|---|---|---|
| DE | 39 12 046 | 3/1990 |
| EP | 0 063 879 A2 | 11/1982 |
| EP | 0 324 474 A1 | 1/1989 |

OTHER PUBLICATIONS

Frame et al (Tetrahedron (1996) 52:9219-9236).*
Randolph, et al., "Stability, specificity and fluorescence brightness of multiply-labeled fluorescent DNA probes," *Nucleic Acids Research*, vol. 25, No. 14, pp. 2923-2929 (1997).

* cited by examiner

*Primary Examiner*—Jeffrey Fredman
(74) *Attorney, Agent, or Firm*—Reed Smith LLP

(57) ABSTRACT

According to the present invention, there is provided a fluorescent nucleotide represented by the formula: A-B-C, wherein A represents a residue of natural or synthetic nucleotide, oligonucleotide, polynucleotide, or derivative thereof, and binds to B at a base moiety in said residue; B represents a divalent linking group or a single bond; and C represents a monovalent group derived from a fluorescent dye having 0 or 1 sulfonic acid group or phosphoric acid group in a molecule. The present invention provides useful fluorescent nucleotides for labeling nucleic acids, specifically, fluorescent nucleotides of which uptake ratio is high in synthetic reaction of nucleic acids.

11 Claims, 1 Drawing Sheet

L1:-Compound 5

L2:-Compound 6

L3:Cy5-dUTP

L1:Cy3-dUTP

L2:-Compound 7

L3:-Compound 8

FLUORESCENT NUCLEOTIDES

FIELD OF THE INVENTION

The present invention relates to a fluorescent nucleotide and its use.

BACKGROUND OF THE INVENTION

One of the most frequently used molecular biological techniques for detecting homologous nucleic acid sequences is DNA/DNA, RNA/RNA, or RNA/DNA hybridization. In this technique, nucleic acid (DNA or RNA) used as a probe is labeled, and the labeled nucleic acid is hybridized to a nucleic acid (DNA or RNA) to be detected. When the nucleic acid used as a probe has a homology to the nucleic acid to be detected, each single-stranded nucleic acid hybridizes to its complementary sequence so as to form a double-stranded sequence, and then the double-stranded sequence is detected by a label of the probe.

Conventionally, when nucleic acid is used as a probe, a technique of labeling the probe with radioisotope has been employed and the presence of hybridization between the probe and a target nucleic acid has been detected by autoradiography.

Although the technique using radioisotopes for labeling a gene probe is especially superior in its high sensitivity, there exist such problems that the handling of radioisotopes is complicated because safety of the laboratory must be ensured and special care must be taken in the disposal of radioactive wastes. Moreover, radioisotopes can be used only for a limited time because they have a half-life period.

For the abovementioned reasons, non-radioactive labeling techniques have been developed as more simple techniques. For example, techniques of labeling a gene probe with biotin molecules (European Patent No. 0 063 879) or with digoxigenin molecules (European Patent Application No. 0 324 474 A1) are known. After hybridization of a labeled nucleic probe to the nucleic acid sequence to be detected, biotin molecules or digoxigenin molecules are present in the resulting double-stranded nucleic acid. After hybridization, binding of (strept)avidin-marker enzyme complex or anti-digoxigenin antibody-marker enzyme complex to the resultant double-stranded nucleic acid sequence allows detection of nucleic acids to which the probes were hybridized. However, such detection methods using enzymes are insufficient in terms of sensitivity and specificity.

Other than the above techniques, various techniques of labeling a target substance with fluorescent dye have been studied. A desired fluorescent labeling reagent (1) possesses a high fluorescent quantum yield, (2) possesses a molecular absorption coefficient, (3) is water-soluble and does not self-quench by agglutinating in an aqueous solvent, (4) is not susceptible to hydrolysis, (5) does not photo-dissociate easily, (6) is not susceptible to background fluorescence, and (7) has a previously introduced reactive substituent which forms covalent binding with a target substance.

Fluorescein isothiocyanate (FITC) and rhodamine isothiocyanate, which are well-known as fluorescent labeling reagents, possess high fluorescent quantum yields, but have drawbacks such that the molecular absorption coefficients are low and the excitation and luminous wavelength is 500 nm to 600 nm and therefore these reagents are susceptible to the influence of background fluorescence of a membrane used for blotting.

As dyes having a high molecular absorption coefficient, for example, polymethine dyes are known such as cyanine dye described in U.S. Pat. No. 5,486,616, Japanese Patent Application Laid-Open Nos. 2-191674, 5-287209, 5-287266, 8-47400, 9-127115, 7-145148 and 6-222059, and barbiturate oxonol described in Journal of Fluorescence, 5, 231, 1995. However, there exist some problems such that they are almost insoluble in water and if they are dissolved, hydrolysis occurs. Also, strong intermolecular interactions between dyes can cause formation of aggregates in an aqueous medium so that self-quenching of fluorescence is often observed.

Moreover, cyanine dyes described in Japanese Patent Application Laid Open No. 2-191674 and the like are superior dyes because they have water-solubility due to introduction of a sulfonic acid group into a relatively stable chromophore and the formation of aggregates is prevented. However, there exist some problems such that uptake efficiency of fluorescent nucleotides is poor by synthetic reactions of nucleic acids, for example, reverse transcription reaction.

SUMMARY OF THE INVENTION

The object of the present invention is to overcome the abovementioned problems in the conventional techniques. Thus, the object of the present invention is to provide a fluorescent nucleotide which is useful for efficient labeling of nucleic acids.

Having conducted intensive study to solve the abovementioned problems, the present inventors prepared a complex of a nucleotide with a fluorescent labeling reagent with low negative charge, and labeled and detected a nucleic acid using the complex. As a result, the inventors have found that the ratio of uptake into the nucleic acid is greatly increased. The present invention has been completed on the basis of this finding.

Thus, according to the present invention, there is provided a fluorescent nucleotide represented by the formula: A-B-C, wherein A represents a residue of natural or synthetic nucleotide, oligonucleotide, polynucleotide, or derivative thereof, and binds to B at a base moiety in the above mentioned residue; B represents a divalent linking group or a single bond; and C represents a monovalent group derived from a fluorescent dye having 0 or 1 sulfonic acid group or phosphoric acid group in a molecule.

According to the present invention, there is further provided a fluorescent nucleotide represented by the formula: A-B-C, wherein A represents a residue of natural or synthetic nucleotide, oligonucleotide, polynucleotide, or derivative thereof, and binds to B at a base moiety in the above mentioned residue; B represents a divalent linking group or a single bond; and C represents a monovalent group derived from a fluorescent dye having a water-soluble group other than a sulfonic acid group, a phosphoric acid group, or a carboxylic acid group in a molecule.

Preferably, the fluorescent dye is a cyanine, merocyanine or styryl fluorescent dye.

Preferably, the cyanine, merocyanine, or styryl fluorescent dye is a fluorescent dye represented by the following formulae,

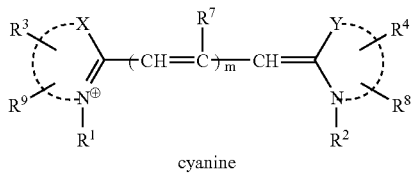
cyanine

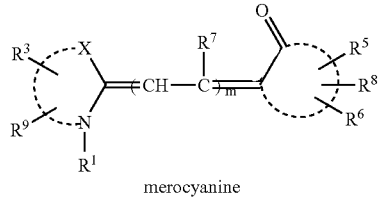
merocyanine

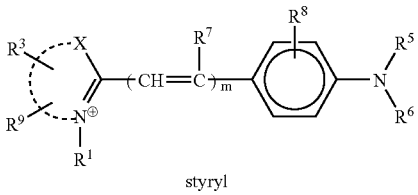
styryl wherein X and Y are each independently selected from the group consisting of O, S, and $C(CH_3)_2$; m is an integer selected from the group consisting of 1, 2, 3 and 4; $R^1$ and $R^2$ each independently represent a hydrogen atom or an alkyl group that may be substituted with a reactive group capable of covalently binding to B, and a oxygen atom or a sulfur atom may be involved in an alkyl chain of the alkyl group, wherein at least one of $R^1$ and $R^2$ represents an alkyl group that may be substituted with a reactive group capable of covalently binding to B; $R^3$ to $R^9$ each independently represent a hydrogen atom or a monovalent substituent, and two adjacent groups thereof may bind to form a ring; and the dashed lines represent carbon atoms required to form the cyanine, merocyanine and styryl fluorescent dyes.

More preferably, the cyanine, merocyanine or styryl fluorescent dye is a fluorescent dye having a structure represented by the following formulae,

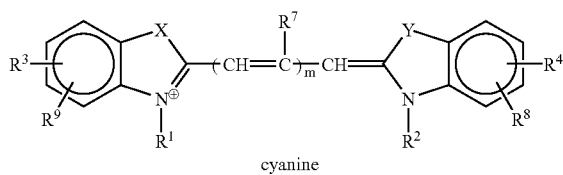
cyanine

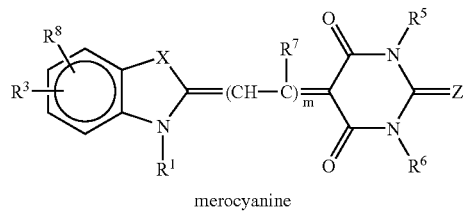
merocyanine

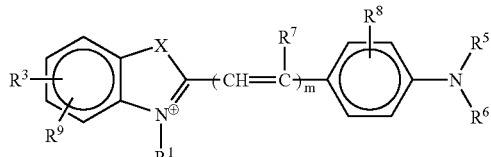
styryl

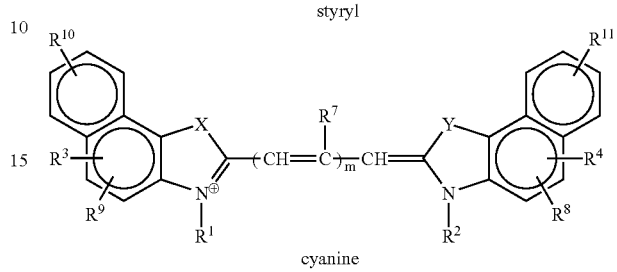
cyanine

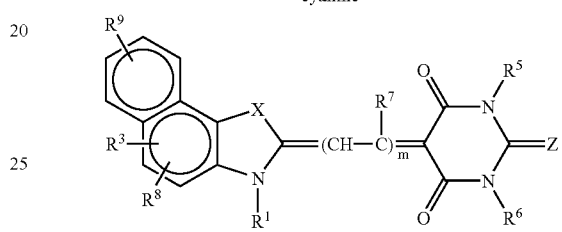
merocyanine

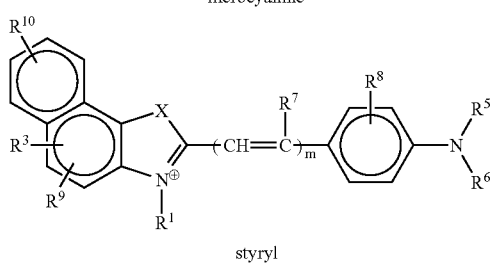
styryl wherein X and Y are each independently selected from the group consisting of O, S, and $C(CH_3)_2$; Z is selected from the group consisting of O and S; m is an integer selected from the group consisting of 1, 2, 3 and 4; $R^1$ and $R^2$ each independently represent a hydrogen atom or an alkyl group that may be substituted with a reactive group capable of covalently binding to B, and an oxygen atom or a sulfur atom may be involved in an alkyl chain of the alkyl group, wherein at least one of $R^1$ and $R^2$ represents an alkyl group that may be substituted with a reactive group capable of covalently binding to B; and $R^3$ to $R^{11}$ each independently represent a hydrogen atom or a monovalent substituent, and two adjacent groups thereof may bind to form a ring.

Preferably, at least one of $R^1$ and $R^2$ is an alkyl group substituted with an active ester group capable of covalently binding to an amino group, a hydroxyl group or a thiol group in the group B.

Preferably, at least one of $R^1$ and $R^2$ is an alkyl group substituted with a carboxyl group.

Preferably, A is a residue of nucleotide or derivative thereof. More preferably, A represents a residue of natural or synthetic nucleotide or derivative thereof selected from (1) the group consisting of nucleotides consisting of AMP, ADP, ATP, GMP, GDP, GTP, CMP, CDP, CTP, UMP, UDP, UTP, TMP, TDP, TTP, 2-Me-AMP, 2-Me-ADP, 2-Me-ATP, 1-Me-GMP, 1-Me-GDP, 1-Me-GTP, 5-Me-CMP, 5-Me-CDP, 5-Me-CTP, 5-MeO-CMP, 5-MeO-CDP, and 5-MeO-CTP;

(2) the group consisting of deoxynucleotides and dideoxynucleotides corresponding to the above-mentioned nucleotides; and (3) the group consisting of derivatives further derived from nucleotides described in the above (1) and (2).

Preferably, B is a linking group consisting of —CH$_2$—, —CH=CH—, —C≡C—, —CO—, —O—, —S—, —NH—, or combinations thereof, wherein a hydrogen atom on the linking group may be further substituted with a substituent.

More preferably, B is an aminoallyl group.

According to another aspect of the present invention, there is provided a process of preparing fluorescence-labeled nucleic acids which comprises the step of conducting a reaction of the synthesis of nucleic acid by using nucleic acid synthetase, a nucleic acid as a template, and the fluorescent nucleotide of the invention.

Preferably, the reaction of the synthesis of nucleic acid is a reaction selected from the group consisting of a reverse transcription reaction, a terminal transferase reaction, a random prime method, a PCR method, or a nick-translation method.

According to further another aspect of the present invention, there is provided a nucleic acid probe or primer which is labeled with the fluorescent nucleotide of the present invention.

According to further another aspect of the present invention, there is provided a diagnostic agent or a reagent for detecting nucleic acids, which consists of the fluorescent nucleotide of the present invention.

According to further another aspect of the present invention, there is provided a kit for detecting nucleic acids comprising (1) the fluorescent nucleotide according to claim 1, (2) a nucleic acid synthetase, and (3) a buffer.

DETAILED DESCRIPTION OF THE INVENTION

Figure 1:
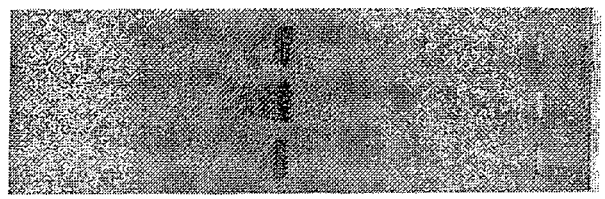
FIG. 1 shows a result of the analysis in which fluorescent dye-labeled DNA probes with indolenine cyanine-dUTP conjugates (Compound 5 and Compound 6) were subjected to agarose gel electrophoresis, and the gel was stained and was scanned by FLA2000 (Fuji Photo Film Co., Ltd.) at 532 nm of excitation wavelength and 580 nm of detection wavelength after staining with SYBR Green II (Molecular Probes).

Embodiments and practices of the present invention will now be described in more detail. The present invention relates to a fluorescent nucleotide represented by the formula: A-B-C.

In the above formula, A represents a residue of natural or synthetic nucleotide, oligonucleotide, polynucleotide or derivative thereof. The natural or synthetic nucleotides include, but are not limited to, residues of natural or synthetic nucleotides or derivative thereof selected from (1) the group consisting of nucleotides consisting of AMP, ADP, ATP, GMP, GDP, GTP, CMP, CDP, CTP, UMP, UDP, UTP, TMP, TDP, TTP, 2-Me-AMP, 2-Me-ADP, 2-Me-ATP, 1-Me-GMP, 1-Me-GDP, 1-Me-GTP, 5-Me-CMP, 5-Me-CDP, 5-Me-CTP, 5-MeO-CMP, 5-MeO-CDP, 5-MeO-CTP, (2) the group consisting of deoxynucleotides and dideoxynucleotides corresponding to the above nucleotides, and (3) the group consisting of derivatives derived from nucleotides described in the above mentioned (1) and (2). Examples of the natural or synthetic nucleotides include, but are not limited to, ATP, CTP, GTP, TTP, UTP, dATP, dCTP, dGTP, dTTP, dUTP, ddATP, ddCTP, ddGTP, ddTTP, ddUTP or the derivatives thereof.

The oligonucleotide is obtained by polymerization of about 1 to 50, preferably 1 to 30, more preferably 1 to 20 nucleotides or derivative thereof as described above, and each nucleotide of constitutive unit may be identical or different. The polynucleotide is a polymer obtained by polymerization of many nucleotides or derivatives thereof as described above, and its size (or length) may be, but is not specifically limited to, several base pairs (bp) to several kbp as the number of bases.

The term "fluorescent nucleotide" used herein is used to mean that it covers all cases in which the nucleic acid components are any of the aforementioned nucleotides, oligonucleotides, and polynucleotides.

A binds to B at a base moiety in the nucleotide residue. Examples of the base moiety of the nucleotide residue include purine derivatives and pyrimidine derivatives. In a purine base, the binding site for the linking group B is not specifically limited as long as it is other than 9-position for binding to a sugar component. For example, where the purine base is adenine, the binding site for the linking group B can be 2- or 8-position, or an amino group present at 6-position; where the purine base is guanine, the binding site can be 1- or 8-position, or an amino group present at 2-position. In a pyrimidine base, a binding site for the linking group B is not specifically limited as long as it is other than 1-position for binding to a sugar component. For example, where the pyrimidine is cytosine, the binding site can be 5- or 6-position, or an amino group present at 4-position; where the pyrimidine base is thymine, the binding site can be 3- or 6-position, or a methyl group present at 5-position; and where the pyrimidine base is uracil, the binding site for the linking group B can be 3-, 5- or 6-position.

In the above formula, B represents a bivalent linking group or a single bond. Types of the linking group are not specifically limited so far as they do not largely affect the characteristics of the fluorescent nucleotide of the present invention (for example, stability of the fluorescent nucleotide as a compound, water-solubility, uptake ratio by nucleic acid, fluorescence intensity and the like). A person skilled in the art can appropriately select a divalent linking group suitable for linking a nucleotide moiety represented by A with a fluorescent compound component represented by C.

In general, the linking group B is a linking group consisting of —CH$_2$—, —CH=CH—, —C≡C—, —CO—, —O—, —S—, —NH—, or combinations thereof, in which a hydrogen atom on the linking group may be further substituted with any substituent. The number of carbons contained in the backbone of the linking group is not specifically limited. Generally, the number of carbons ranges from 1 to 50, preferably 1 to 20, more preferably 1 to 10, most preferably 1 to 5.

In the above formula, C represents (1) a monovalent group derived from a fluorescent dye having 0 or 1 sulfonic acid group or phosphoric acid group in a molecule (particularly preferably, cyanine, merocyanine or styryl fluorescent dye) or (2) a monovalent group derived from a fluorescent dye having water-soluble group(s) other than a sulfonic acid group, phosphoric acid group, or carboxylic acid group in a molecule (particularly preferably, cyanine, merocyanine or styryl fluorescent dye).

As fluorescent dyes which give a monovalent group represented by C, for example, a cyanine, merocyanine or styryl fluorescent dye is preferable. For example, known dyes described in Japanese Patent Laid-Open No. 9-124599 can be used. An indocyanine compound having no sulfonic acid group is described in Japanese Patent Laid-Open 9-124599, but it is not discussed that a sulfonic acid group contributes reduction of intake efficiency by nucleic acid in synthetic reaction of nucleic acid such as reverse transcription reaction. The present invention is characterized in that functional groups having negative charges such as a sulfonic acid group and phosphoric acid group were reduced as possible in design for a optimal molecular structure of the fluorescent nucleotide for the purpose of reducing repulsion among molecules having negative charges because nucleic acid molecules have negative charges. Namely, in one embodiment of the present invention, the fluorescent dye is characterized in that the number of sulfonic acid group or phosphoric acid group present in the fluorescent dye component is 0 or 1.

However, especially fluorescent dyes of high molecular weights sometimes become to be insoluble due to reduction of functional groups having theses negative charges. In one aspect of the present invention, the problem for these insolubility is solved by introducing a water-soluble functional group into a chromophore of a dye. For example, in one embodiment of the present invention, the fluorescent nucleotide is characterized in that it has a water-soluble group other than a sulfonic acid group in its fluorescent dye component. Water-soluble functional groups which can be introduced into the fluorescent dye include sulfonamide, polyether, lower alcohol, sugar chain, tertiary amine, quaternary ammonium salt and the like.

The fluorescent dye used herein is preferably cyanine, merocyanine, or styryl fluorescent dye. Preferably specific structures of cyanine, merocyanine, or styryl fluorescent dye include, for example, the structures represented by the following formulae:

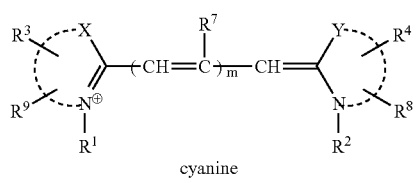
cyanine

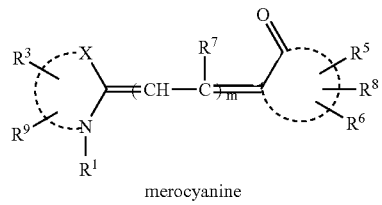
merocyanine

-continued

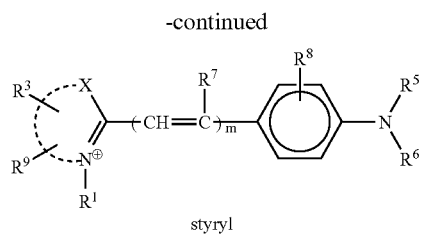
styryl wherein X and Y are each independently selected from the group consisting of O, S, and $C(CH_3)_2$; m is an integer selected from the group consisting of 1, 2, 3, and 4; $R^1$ and $R^2$ each independently represent a hydrogen atom, or an alkyl group which may be substituted with a reactive group capable of covalently binding to B, wherein an oxygen atom or a sulfur atom may be involved in an alkyl chain of the alkyl group, and at least one of $R^1$ and $R^2$ represents an alkyl group which may be substituted with a reactive group capable of covalently binding to B; $R^3$ to $R^9$ each independently represent a hydrogen atom, or a monovalent substituent, and two adjacent groups thereof may bind to form a ring. The dashed lines represent carbon atoms required for formation of the aforementioned cyanine, merocyanine, or styryl fluorescent dye.

More preferably specific structures of cyanine, merocyanine, or styryl fluorescent dye include, for example, the structures represented by the following formulae:

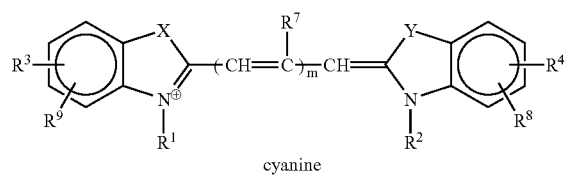
cyanine

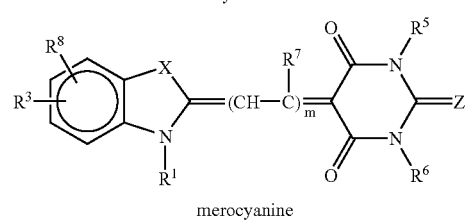
merocyanine

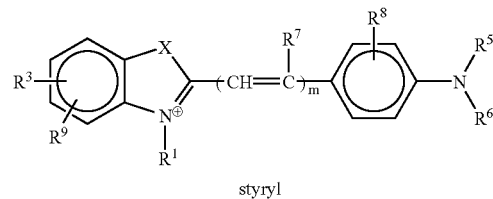
styryl

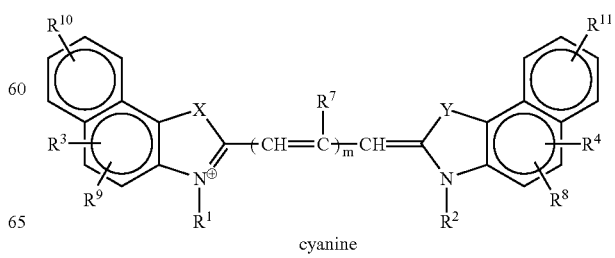
cyanine

-continued

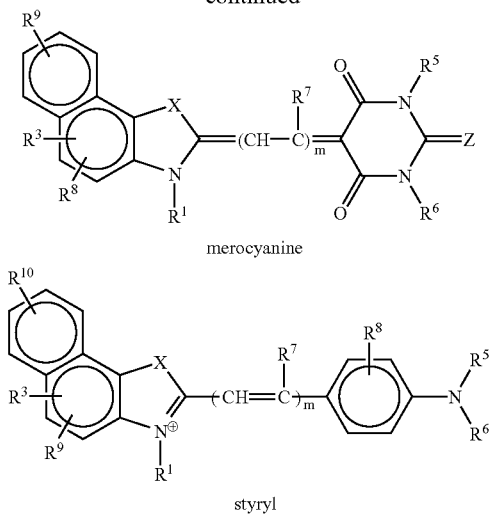

merocyanine styryl wherein X and Y are each independently selected from the group consisting of O, S, and $C(CH_3)_2$; Z is selected from the group consisting of O and S; m is an integer selected from the group consisting of 1, 2, 3, and 4; $R^1$ and $R^2$ each independently represent a hydrogen atom, or an alkyl group which may be substituted with a reactive group capable of covalently binding to B, in which an oxygen atom or a sulfur atom may be involved in an alkyl chain of the alkyl group, and at least one of $R^1$ and $R^2$ represents an alkyl group which may be substituted with a reactive group capable of covalently binding to B; $R^3$ to $R^{11}$ each independently represent a hydrogen atom, or a monovalent substituent, and two adjacent groups thereof may bind to form a ring.

As used herein, an alkyl group may be straight chain, branched chain, ring chain, or a combination thereof and contains from about 1 to 20 carbon atoms unless otherwise specified. Alkyl groups represented by $R^1$ and $R^2$ may be identical or different. Examples of such alkyl groups can include a methyl group, an ethyl group, an n-propyl group, an isopropyl group, a cyclopropyl group, an n-butyl group, a sec-butyl group, a tert-butyl group, a cyclopropylmethyl group, an n-pentyl group, an n-hexyl group, a cyclohexyl group and the like. Alkyl groups represented by $R^1$ and $R^2$ may have one or more substituents at any position on the alkyl chains. When the alkyl group contains two or more substituents, the substituents may be identical or different.

The types of the substituents on the alkyl groups represented by $R^1$ and $R^2$ are not specifically limited. It is preferred that a reactive substituent capable of forming covalent bond, ion bond, hydrogen bond and the like with a nucleotide (or a linking group binding to a nucleotide), is incorporated in order to introduce a fluorescent dye of the above formula into the nucleotide as a fluorescent label (The term "reactive substituent" as used herein means a substituent having the above mentioned characteristics.).

Examples of reactive substituents which can be incorporated into each of the alkyl group represented by $R^1$ and $R^2$ can include a succinimidyl ester group, a halogen-substituted toriazinyl group, a halogen-substituted pyrimidinyl group, a sulfonyl halide group, an α-haloacetyl group, a maleimidyl group, and an aziridinyl group. In addition to these reactive substituents, examples of the reactive substituents further include a halogen atom (the term "halogen atom" used herein may be any of a fluorine atom, a chlorine atom, a bromine atom, and an iodine atom), a mercapto group, a cyano group, a nitro group, a carboxyl group, a phosphoric acid group, a sulfo group, a hydroxyl group, an amino group an isothiocyanate group, an isocyanate group, an alkoxyl group having carbon number of 1 to 8 (e.g., a methoxy group and ethoxy group), an aryloxy group having carbon number of 6 to 20 (e.g., a phenoxy group, and a naphthoxy group), an alkoxycarbonyl group having carbon number of 2 to 10 (e.g., a methoxycarnonyl group, and an ethoxycarbonyl group), an aryloxycarbonyl group having carbon number of 6 to 20 (e.g., phenoxycarbonyl group), an acyl group having carbon number of 2 to 10 (e.g., an acetyl group and a pivaloyl group), an acyloxy group having carbon number of 2 to 8 (e.g., an acetyloxy group and a benzoyloxy group), an acylamino group having carbon number of 2 to 8 (e.g., an acetylamino group), a sulfonyl group having carbon number of 1 to 8 (e.g., a methanesulfonyl group, an ethanesulfonyl group, and a benzenesulfonyl group), a sulfinyl group having carbon number of 1 to 20 (e.g., a methanesulfinyl group, an ethanesulfinyl group, and a benzenesulfinyl group), a sulfonylamino group having carbon number of 1 to 8 (e.g., a methanesulfonyl amino group, an ethanesulfonylamino group, and a benzenesulfonylamino group), a carbamoyl group having carbon number of 1 to 10 (e.g., a carbamoyl group, a methylcarbamoyl group, and a morpholinocarbamoyl group), a substituted amino group having carbon number of 1 to 20 (e.g., a methylamino group, a dimethyl amino group, a benzyl amino group, an anilino group, and a diphenylamino group), a sulfamoyl group having carbon number of 2 to 10 (e.g., a methylsulfamoyl group, an ethylsulfamoyl group, and a piperidinosulfamoyl group), an ammonium group having carbon number of 0 to 15 (e.g., a trimethyl ammonium group, and a triethyl ammonium group), a hydrazino group having carbon number of 0 to 15 (e.g., a trimethyl hydrazino group), an ureido group having carbon number of 1 to 15 (e.g., an ureido group, and an N,N-dimethyl ureido group), an imide group having carbon number of 1 to 15 (e.g., succinimide group), an alkylthio group having carbon number of 1 to 20 (e.g., a methylthio group, and an ethylthio group), an arylthio group having carbon number of 6 to 20 (e.g., a phenylthio group, a p-methylphenylthio group, a p-chlorophenylthio group, a 2-pyridythio group, and a naphthylthio group), a substituted or unsubstituted heterocyclic group having carbon number of 1 to 20 (e.g., a pyridyl group, a 5-methyl pyridyl group, a thienyl group, a furyl group, a morpholino group, a tetrahydrofuryl group, and a 2-pyradyl group), a saturated carbohydrate group having carbon number of 2 to 18 (e.g., a vinyl group, an ethynyl group, a 1-cyclohexenyl group, a benzylidine group, and a benzylidene group), a substituted or unsubstituted aryl group having carbon number of 6 to 20 (e.g., a phenyl group, a 4-sulfophenyl group, a 2,5-disulfophenyl group, a 4-carboxyphenyl group, and a naphthyl group), and an alkyl group having carbon number of 1 to 20 (e.g., a methyl group, an ethyl group, and a propyl group).

Preferred examples of $R^1$ and $R^2$ can include an alkyl group having carbon number of 1 to 15 which is substituted with a carboxyl group, an isothiocyanate group, a succinimidyl ester group, a sulfonyl halide group, an α-haloacetyl group, or a maleimidyl group; and an arylalkyl group having carbon number of 7 to 20 which is substituted with a carboxyl group, an isothiocyanate group, a succinimidyl ester group, a sulfonyl halide group, an α-haloacetyl group, or a maleimidyl group. More preferred examples of $R^1$ and $R^2$ include an alkyl group having carbon number of 1 to 10 which is substituted with a carboxyl group, an isothiocyanate group, or a succinimidyl ester group.

$R^3$ to $R^{11}$ each independently represent a hydrogen atom, or a monovalent substituent, and two adjacent groups thereof may bind to form a ring.

The types of substituents represented by $R^3$ to $R^{11}$ are not specifically limited, and may be identical or different. The substituents represented by these groups inlude, for example, those exemplified as substituents on the alkyl groups represented by $R^1$ and $R^2$ (including reactive substituents).

Two adjacent groups among $R^3$ to $R^{11}$ may be combined with each other to form a saturated or unsaturated ring. The thus-formed ring includes 5- to 7-membered rings. An unsaturated ring may form a condensed aromatic ring. The unsaturated ring may contain a hetero atom(s) such as an oxygen atom, a nitrogen atom, and a sulfur atom. At any position on the formed ring, one or more substitutions illustrated as those on the alkyl groups represented by $R^1$ and $R^2$ or alkyl groups may be substituted.

Preferred examples of $R^3$ to $R^{11}$ include, for example, a hydrogen atom, a halogen atom (fluorine atom, chlorine atom, bromine atom, or iodine atom), $-SO_2NH_2$, an alkyl group having carbon number of 1 to 6 (in which a substituent including reactive substituents, as illustrated as those on the alkyl groups represented by $R^1$ and $R^2$, may be substituted at any position), an aryl group having carbon number of 6 to 20 (in which a substituent including reactive substituent, as illustrated as those on the alkyl groups represented by $R^1$ and $R^2$, may be substituted at any position), a thioalkyl group having carbon number of 1 to 10, an alkylsulfone group having carbon number of 1 to 10, an alkoxy group having carbon number of 1 to 10, a substituted amino group, an isothiocyanate group, an isocyanate group, a succinimidyl ester group, a halogen-substituted triazinyl group, a halogen-substituted pyrimidinyl group, a sulfonyl halide group, an α-haloacetyl group, a maleimidyl group, an aziridinyl group, monochlorotriazine, dichlorotriazine, mono- or di-halogen-substituted pyridine, mono - or di-halogen substituted diazine, acid halide, hydroxy succinimide ester, hydroxy sulfo succinimide ester, imido ester, hydrazine, azidenitrophenyl, azide, 3-(2-pyrizyldithio) propionamide, glyoxal and aldehyde.

In the present invention, at least one of $R^3$ to $R^9$, or at least one of $R^3$ to $R^{11}$ is preferably other than a hydrogen atom.

The fluorescent dye mentioned above is used as a fluorescence labeling component in the fluorescent nucleotide of the present invention.

Various techniques are known for introducing a fluorescent dye into a nucleotide as a fluorescent label, and can be used by appropriately selecting means available for a skilled person in the art. For example, a functional group such as an amino group or a hydroxyl group in the nucleotide may be directly bound to a reactive substituent such as a carboxyl group or an active ester group in the fluorescent dye via ion bond or covalent bond; or after chemical modification such as incorporation of a linking group into a part of the nucleotide, the fluorescent dye may be allowed to be reacted.

The fluorescent nucleotide produced after reaction can be purified by a general separation technique, such as chromatography, electrophoresis and re-crystallization.

The present invention further relates to the use of the fluorescent nucleotide of the present invention. Namely, the fluorescent nucleotide of the present invention can be used for detecting nucleic acids.

When the fluorescent nucleotide of the present invention is used for DNA analysis such as detection of nucleic acids, the fluorescent nucleotide of the present invention can be incorporated into a probe or a primer by Ruth's technique (Jerry L. Ruth, DNA, 3, 123, 1984). The present invention further provides a process of preparing fluorescence-labeled nucleic acids which comprises the step of conducting a reaction of the synthesis of nucleic acid by using nucleic acid synthetase, a nucleic acid as a template, and the fluorescent nucleotide of the present invention.

Examples of nucleic acid synthetase used herein include, but are not limited to, DNA polymerase (including any DNA polymerase, such as Klenow enzyme, Taq DNA polymerase and the like), RNA polymerase, reverse transcriptase, or terminal transferase. The types of a nucleic acid as a template may be DNA or RNA, and may be natural DNA or RNA, recombinant DNA or RNA, or chemically-synthesized DNA or RNA. The reaction of the synthesis of nucleic acid may be performed under conditions (e.g., salt concentration, pH, and temperature) suitable for enzymatic reaction using template DNA, non-fluorescent nucleotide mixture, the fluorescent nucleotide of the present invention and the nucleic acid synthetase. The methods of synthesizing nucleic acid are well-known to a person skilled in the art. A person skilled in the art can appropriately select substances and reagents used according to their purposes for labeling.

Various methods can be used to label nucleic acid (DNA or RNA) using the fluorescent nucleotide of the present invention.

The random prime method is one of the methods for labeling DNA, wherein a mixture of optionally combined hexanucleotide sequences is used as a primer (i.e., random primer), and the random primer is hybridized to a nucleic acid to be labeled. Starting from 3'-OH terminus of this random primer, a strand complementary to the single strand is synthesized using a DNA polymerase such as Klenow enzyme, or other DNA polymerase. At that time, 4 types of deoxyribonucleotide, each of which is a substrate of DNA polymerase, are introduced into the complementary strand. By using the fluorescent nucleotide of the present invention as at least one type of these deoxyribonucleotide, complementary DNA labeled with the fluorescent nucleotide is synthesized.

Instead of a random primer, oligo DNA having a specific sequence (specific primer) can be used. The specific primer binds to a complementary region in a template DNA, then the synthesis of DNA complementary to the template DNA starts from the 3'-OH terminus of the specific primer. As in the case of the random prime method, the fluorescent nucleotide of the present invention is incorporated during the synthesis of complementary DNA, thereby fluorescence-labeled complementary DNA is synthesized.

Nick translation is a method using the action of DNase I on double-stranded DNA. The action of DNase I creates a cleavage site at which the template double-stranded DNA is cut into a single strand. Simultaneously, *E. coli* DNA polymerase I, 4 types of deoxyribonucleotides that are substrates of this enzyme, and the fluorescent nucleotide of the present invention are added to the reaction mixture. *E. coli* DNA polymerase I cleaves a 5'-terminal deoxyribonucleotide of the cleaved single strand and simultaneously inserts one substrate deoxyribonucleotide at a site adjacent to the free 3'-OH terminus. By repeating this process, the cleavage site moves toward the 3' terminus. By containing the fluorescent nucleotide of the present invention in the substrate nucleotide, fluorescent DNA can be synthesized by nick translation.

To label the 3' terminus of double- or single-stranded DNA, terminal transferase, which is an enzyme to bind a deoxyribonucleotide or ribonucleotide to the 3′-OH terminus, can be used. The terminal transferase requires at least one type of deoxyribonucleotide or ribonucleotide as a substrate. By using the fluorescent nucleotide of the present invention as a substrate for the terminal transferase, fluorescence-labeled nucleic acids elongating from 3′-OH terminus can be synthesized.

Reverse transcription is a reaction to synthesize complementary DNA from a single-stranded RNA. After annealing an oligo deoxyribonucleotide as a primer to a complementary portion of RNA, an elongation reaction is performed using reverse transcriptase, thereby synthesizing DNA strand complementary to RNA strand starting from the 3′-OH terminus of the primer. In this DNA synthesis, four types of deoxyribonucleotides are used as substrates for enzymes. The use of the fluorescent nucleotide of the present invention as one of these substrates allows the fluorescent nucleotide to be inserted into elongating DNA strand during reverse transcription so that fluorescence-labeled DNA is synthesized.

RNA labeled with the fluorescent nucleotide of the present invention can be synthesized using an enzyme that synthesizes RNA from DNA. Such enzymes that synthesize RNA from DNA include RNA polymerase encoded by a phage, such as SP6, T3 or T7 RNA polymerase. These enzymes are those for the synthesis of double-stranded DNA and RNA containing SP6, T3 or T7 promoter, and four types of ribonucleotides are used as substrates. By using the fluorescent nucleotide of the present invention as one of the substrates, fluorescence-labeled RNA can be synthesized.

Alternatively, nucleic acids labeled with the fluorescent nucleotide of the present invention can be synthesized by polymerase chain reaction (PCR). In PCR, nucleic acids to be detected in the biological sample are denatured into a single strand, and two types of primers are annealed to the single-stranded nucleic acids. After annealing, elongation reaction is conducted using polymerase (preferably Taq DNA polymerase) and deoxyribonucleotides as enzyme substrates. Complementary DNA is synthesized starting from 3′-OH terminus of the primer, thereby forming double-stranded DNA. By repeating this process, DNA to be detected in the sample can be amplified. By using the fluorescent nucleotide of the present invention as one of the substrates during elongation reaction by Taq DNA polymerase, fluorescence-labeled nucleotides can be amplified.

Fluorescent nucleic acids labeled with the fluorescent nucleotide of the present invention prepared as described above can be used as gene probes for detecting homologous nucleic acid sequences by hybridization. Fluorescent nucleotide to which a target nucleic acid was hybridized, can be easily detected by measuring the fluorescence intensity using a fluorometer.

As described above, the fluorescent nucleotide of the present invention is useful as a diagnostic agent or as a reagent for detecting nucleic acids since the fluorescent nucleotide of the present invention can be used for labeling gene probes.

When the fluorescent nucleotide of the present invention is used as a diagnostic agent or as a reagent for detecting nucleic acids, it can be supplied in the form of a reagent composition in combination with one or more types of additives. For example, the reagent can be prepared in a desired form such as a solution, using a proper additive(s), including a buffer, a solubilizer, a pH modifier, and a preservative. A person skilled in the art can appropriately select the form of reagent and the process for the preparation thereof.

Furthermore, the fluorescent nucleotide of the present invention can be supplied in the form of a kit for detecting nucleic acids, together with an enzyme usable in the above described nucleic acid synthetic reaction, a buffer and the like. Types of reagents to be contained in the kit can be appropriately selected according to the purpose of the kit. Such reagent may include the fluorescent nucleotide, nucleic acid synthetase, buffer, as well as a mixture of one or more (preferably four) non-fluorescent nucleotides, purified water, or the like. The kit can further contain primers, such as random primers, oligo dT primer or specific primers according to purposes.

The disclosure of Japanese Patent Application No. 2000-107675 filed on Apr. 10, 2000 on which the present application claims a priority, is herein incorporated by reference.

The present invention is further described in the following examples. These examples are not intended to limit the scope of the invention. Those skilled in the art will realize that various changes, modifications, or substitutions of materials and methods described in examples may be made without departing from the spirit of the invention.

EXAMPLES

The structures of the compounds (Compounds 1–8) synthesized and used in examples are shown below.

compound 1

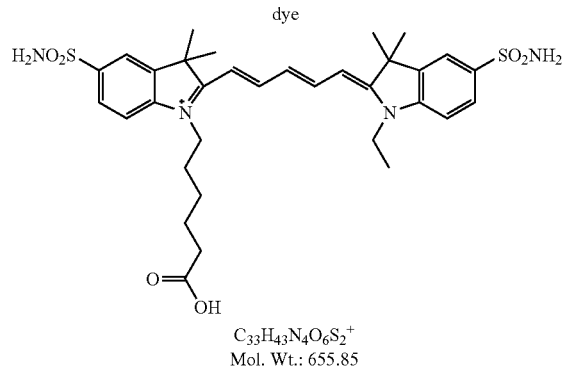

$C_{33}H_{43}N_4O_6S_2^+$
Mol. Wt.: 655.85

-continued
compound 2
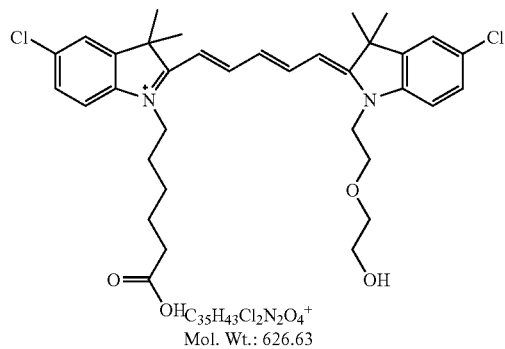
$C_{35}H_{43}Cl_2N_2O_4^+$
Mol. Wt.: 626.63
compound 3
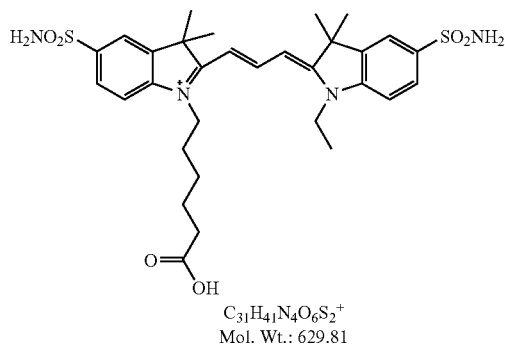
$C_{31}H_{41}N_4O_6S_2^+$
Mol. Wt.: 629.81
compound 4
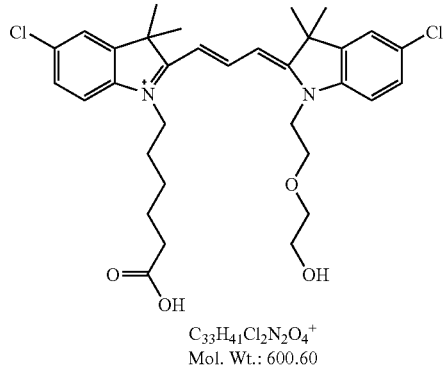
$C_{33}H_{41}Cl_2N_2O_4^+$
Mol. Wt.: 600.60

-continued
dye-dUTP
compound 5
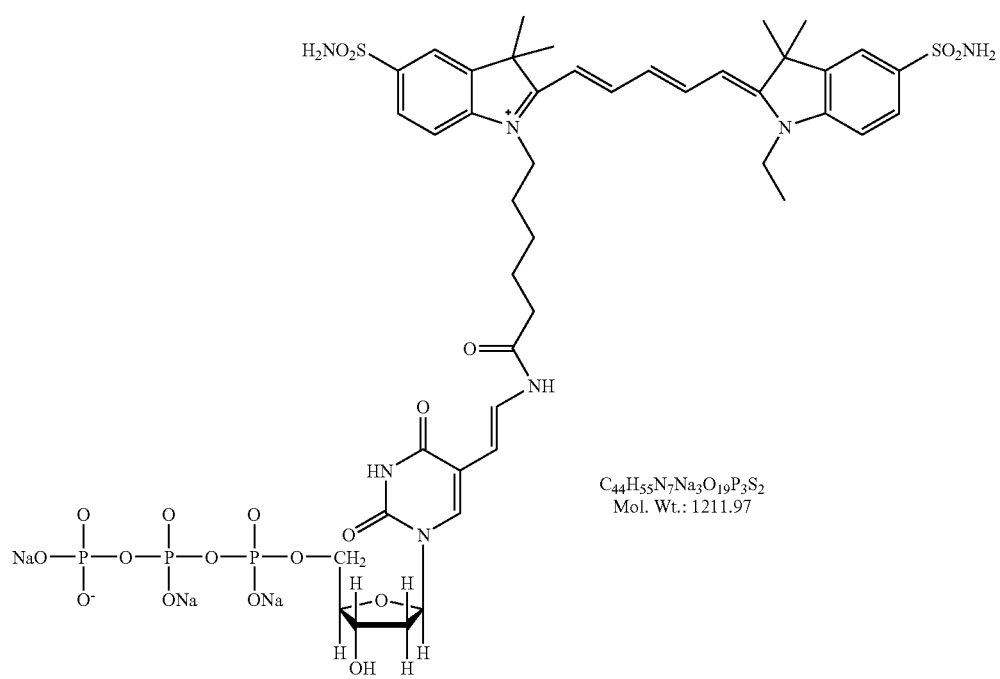
C$_{44}$H$_{55}$N$_7$Na$_3$O$_{19}$P$_3$S$_2$
Mol. Wt.: 1211.97
compound 6
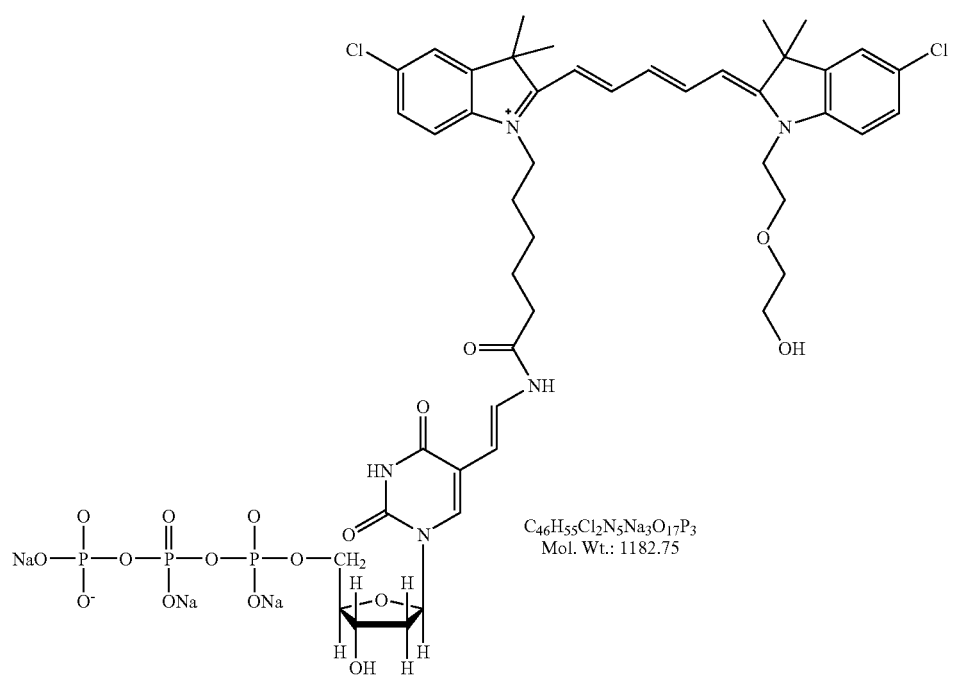
C$_{46}$H$_{55}$Cl$_2$N$_5$Na$_3$O$_{17}$P$_3$
Mol. Wt.: 1182.75

-continued

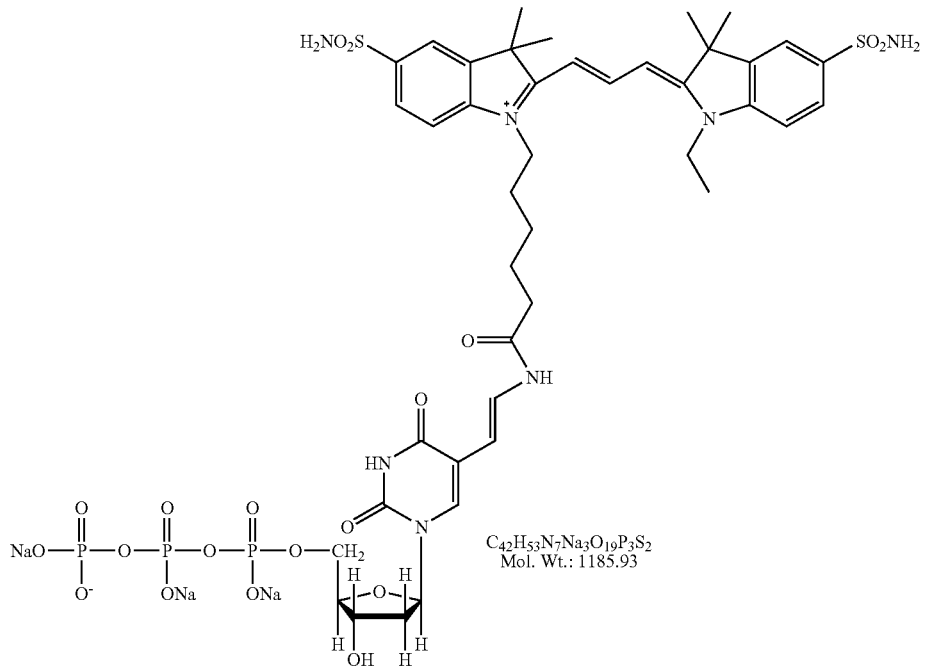

compound 7

$C_{42}H_{53}N_7Na_3O_{19}P_3S_2$
Mol. Wt.: 1185.93

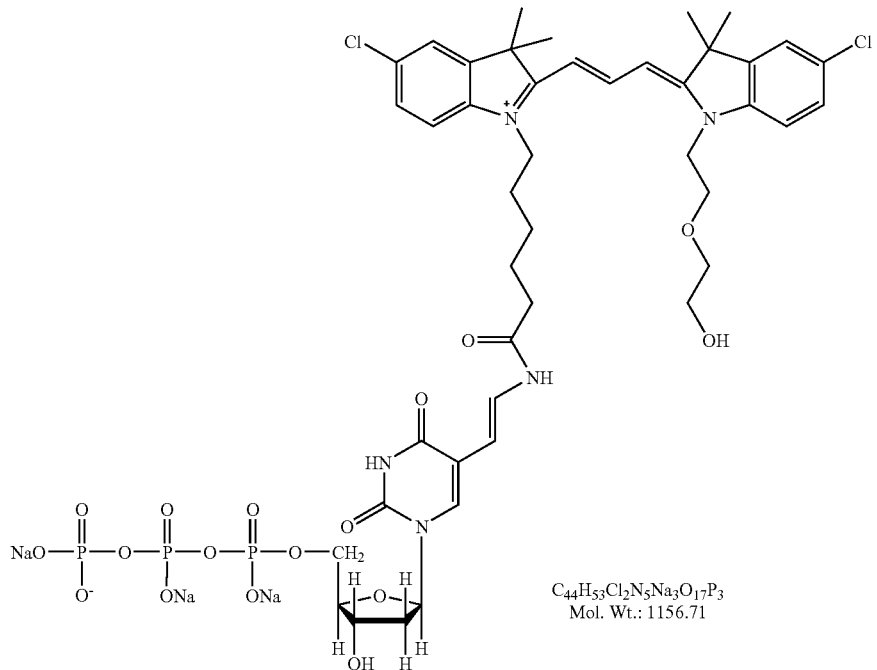

compound 8

$C_{44}H_{53}Cl_2N_5Na_3O_{17}P_3$
Mol. Wt.: 1156.71

Example A

Synthesis of Compound 1 to 4

The compounds used herein were synthesized from 2,3,3-trimethyl indolenine derivative as a source material which was synthesized from commercially available 4-substituted aniline derivative (4-chloroaniline, 4-amino-benzenesulfonamide) according to the method of Fisher et al (E. Fisher, O. Hess, Berichte, 17:559(1883).

(Synthesis of Compound 1)

A large excess amount of ethyl iodine was added to 9.5 g (0.04 mol) of 2,3,3-trimethyl indolenine-5-sulfonamide, and the mixture was refluxed for 24 hours. After removing excess ethyl iodine by decantation, and washing with acetone repeatedly, N-ethyl-2,3,3-trimethyl indolenium-5-sulfonamide iodine salt (Compound A) was obtained. The amount was 6.8 g and the yield was 42%

6-Bromohexanoic acid (9.8 g, 0.05 mol) and 1,2-dichlorobenzene (100 ml) were added to 2,3,3-trimethyl indolenine-5-sulfonamide (9.5 g, 0.04 mol), and the mixture was heated at 110° C. for 12 hours. After cooling down, the reaction solution was concentrated under vacuum, and then purified by a silica gel column chromatography (methanol/chloroform) to give 1-(5-carboxypentynyl)-2,3,3-trimethyl indolenium-5-sulfonamide bromine salt (Compound B). The amount was 9.0 g and the yield was 52%.

Compound A (2.0 g, 0.005 mol) and Compound B (2.2 g, 0.005 mol) were dissolved in 10 ml of pyridine, and the mixture was heated at 110° C. for 1 hour. Then, 1.0 g of 1,3,3-trimethoxypropene (0.0075 mol) was added and the mixture was reacted under heating for 1 hour. The reaction solution was concentrated under vacuum, dissolved in chloroform, and then washed with water. After the solution was dried and concentrated, purification on silica gel column chromatography gave the objective Compound 1 as a black green powder. The amount was 660 mg and the yield was 20%.

(Synthesis of Compound 2)

6-Bromohexanic acid (9.8 g, 0.05 mol) and 1,2-dichlorobenzene (100 ml) were added to 2,3,3-trimethyl indolenine-5-chloride (7.7 g, 0.04 mol), and the mixture was heated at 110° C. for 12 hours. After cooling down and concentration under vacuum, the residue was purified by a silica gel column chromatography (methanol/chloroform) to give 2,3,3-trimethyl indolenium-5-chloride bromine salt. The amount was 9.3 g and the yield was 60%.

Iodoethoxy ethanol (which was synthesized via a halogen exchange by refluxing chloroethoxy ethanol in acetone in the presence of NAI) (10.8 g, 0.05 mol) and 1,2-dichlorobenzene (100 ml) were added to 2,3,3-trimethyl indolenine-5-chloride (7.7 g, 0.04 mol), and the mixture was heated at 110° C. for 12 hours. After cooling down and concentration under vacuum, the residue was purified by a silica gel column chromatography (methanol/chloroform) to give 1-(2-hydroxyethoxyethyl)-2,3,3-trimethyl indolenium-5-chloride iodine salt (Compound D). The amount was 7.7 g and the yield was 47%.

Compound C (1.6 g, 0.005 mol) and Compound D (1.4 g, 0.005 mol) were dissolved in 10 ml of pyridine, and the mixture was heated to 110° C. Then, 1,3,3-trimethoxypropene (1.0 g, 0.0075 mol) was added and reacted under heating for 1 hour. After concentration under vacuum, the reaction solution was dissolved in chloroform, and washed with water. The solution was dried and concentrated, and the purified by a silica gel column chromatography to give the objective Compound 2 as a black green powder. The amount was 490 mg and the yield was 16%.

(Synthesis of Compound 3)

Compound A (2.0 g, 0.005 mol) and Compound B (2.2 g, 0.005 mol) were dissolved in 10 ml of pyridine and the mixture was heated to 110. C. Then, triethyl orthoformate (1.1 g, 0.0075 mol) was added and reacted under heating for 1 hour. After concentration under vacuum, the reaction solution was dissolved in chloroform, and washed with water. The solution was dried and concentrated, and then was purified by a silica gel column chromatography (methanol/chloroform) to give the objective Compound 3 as a black brown powder. The amount was 710 mg and the yield was 23%.

(Synthesis of Compound 4)

Compound C (1.6 g, 0.005 mol) and Compound D (1.4 g, 0.005 mol) were dissolved in 10 ml of pyridine and the mixture was heated to 110° C., and then triethyl orthoformate (1.1 g, 0.0075 mol) was added and reacted under heating for 1 hour. The reaction solution was concentrated under vacuum, dissolved in chloroform, and washed with water. Then, the solution was dried, concentrated, and purified by a silica gel column chromatography (methanol/chloroform) to give the objective Compound 4 as a black brown powder. The amount was 540 mg and the yield was 18%.

Example B

Synthesis of Compounds 5 to 8

By using indolenine cyanine of Compounds 1 to 4, dUTP-conjugates of each Compound (Compounds 5 to 8) were synthesized.

(Synthesis of Compound 5)

1 ml of acetonitrile and 2 ml of 0.1 M MES buffer were added to 5.75 mg (1.0 parts) of Compound 1 to dissolve it, and then 2.20 mg (1.2 parts) of WSC hydrochloride and 2.52 mg (1.2 parts) of Sulfo-NHS were added thereto followed by stirring at room temperature for 30 minutes. After adding thereto 2.2 mg of aminoallyl-dUTP (Sigma) dissolved in 200 µl of 0.1 M MES buffer, a reaction was carried out at room temperature overnight. After adding 100 µl of 1 M Tris buffer (pH 7.5) and stopping the reaction, the resultant reaction solution was absorbed on a column in which 8 g of ODS silica (YMC-ODS-AQ 120A) was previously filled, and was eluted with 30% methanol aqueous solution. After the eluant is concentrated, it was further purified by intermediate pressure preparative chromatography (YAMAZEN Ultrapack ODS-S-40B) to obtain Compound 5 with 95% purity (Yield: 63%).

MS analysis value: M-1211

(Synthesis of Compound 6)

5.40 mg (1.0 parts) of Compound 2 was dissolved in 400 µl of DMSO, and then 1.86 mg (1.2 parts) of WSC hydrochloride and 2.13 mg (1.2 parts) of Sulfo-NHS were added thereto followed by stirring at room temperature for 30 minutes. After adding thereto 2.2 mg of aminoallyl-dUTP (Sigma) dissolved in 2 ml of 0.1 M MES buffer, reaction was carried out at room temperature overnight. After adding 100 µl of 1 M Tris buffer (pH 7.5) and stopping the reaction, the resultant reaction solution was absorbed on a column in which 8 g of ODS silica (YMC-ODS-AQ 120A) was previously filled, and was eluted with 40% methanol aqueous solution. After the eluant is concentrated, it was further purified by intermediate pressure preparative chromatography (YAMAZEN Ultrapack ODS-S-40B) to obtain Compound 6 with 92% purity (Yield: 56%).

MS analysis value: M-1182

(Synthesis of Compound 7)

5.40 mg (1.0 parts) of Compound 3 was dissolved in 400 µl of DMSO, and then 1.86 mg (1.2 parts) of WSC hydrochloride and 2.13 mg (1.2 parts) of Sulfo-NHS were added thereto followed by stirring at room temperature for 30 minutes. After adding thereto 2.2 mg of aminoallyl-dUTP (Sigma) dissolved in 2 ml of 0.1 M MES buffer, reaction was carried out at room temperature overnight. After adding 100 µl I of 1 M Tris buffer (pH 7.5) and stopping the reaction, the resultant reaction solution was absorbed on a column in which 8 g of ODS silica (YMC-ODS-AQ 120A) was previously filled, and was eluted with 40% methanol aqueous solution. After the eluant is concentrated, it was further purified by intermediate pressure preparative chromatography (YAMAZEN Ultrapack ODS-S-40B) to obtain Compound 7 with 92% purity (Yield: 49%).

MS analysis value: M-1185

(Synthesis of Compound 8)

2.16 mg (1.0 parts) of Compound 4 was dissolved in 200 µl of DMSO, and then 0.76 mg (1.1 parts) of WSC hydrochloride and 0.86 mg (1.1 parts) of Sulfo-NHS were added thereto followed by stirring at room temperature for 30 minutes. After adding thereto 2.2 mg of aminoallyl-dUTP (Sigma) dissolved in 1 ml of 0.1 M MES buffer, reaction was carried out at room temperature overnight. After adding 100 µl of 1 M Tris buffer (pH 7.5) and stopping the reaction, the resultant reaction solution was absorbed on a column in which 8 g of ODS silica (YMC-ODS-AQ 120A) was previously filled, and was eluted with 40% methanol aqueous solution. After the eluant is concentrated, it was further purified by intermediate pressure preparative chromatography (YAMAZEN Ultrapack ODS-S-40B) to obtain Compound 8 with 95% purity (Yield: 67%).

MS analysis value: M-1156

Example C

Preparation of Fluorescent Dye-labeled DNA Probe

Example C-1

Preparation of Fluorescent Dye-labeled DNA Probe using Indolenine Cyanine-dUTP Conjugate cRNA was prepared by acting T7 RNA polymerase on pBlueScriptIISK(+)-α-2-HS-glycoprotein as a template (MEGAscript, Ambion). RNaseOUT (Gibco BRL) (40 U), dATP (500 µM), dGTP (500 µM), dCTP (500 µM), dTTP (200 µM), Compound 5 or Compound 6 (100 µM) obtained in Example B, SuperScript II reverse transferase (Gibco BRL) (400 U), and DEPC-treated water (up to total volume of 20 µl) were added to a mixture of cRNA and Primer 1 (SEQ ID NO. 1: TGGCCGCCTTCAACGCTCAG), and the mixture was reacted at 42° C. for 2 hours.

After completion of the reaction, the reaction was stopped and cRNA was decomposed by adding EDTA and NaOH and incubating the mixture at 65° C. for 1 hour. The reaction solution was passed through CentriSep column (PRINCETON SEPARATION, INC) to remove unreacted Compound 5 or Compound 6 for purification.

For comparison, the reverse transcription reaction was carried out in the same way as stated above by using the fluorescent nucleotide labeled with Cy 5 (Cy 5-dUTP conjugate; Amersham Pharmacia Biotech) instead of Compound 5 or Compound 6, and the obtained reaction product was purified.

After the purification, each of the reaction solution was subjected to agarose gel electrophoresis. The gel was stained with SYBR Green II (Molecular Probes), and was scanned by FLA2000 (Fuji Photo Film Co., Ltd.) at 633 nm of excitation wavelength and 675 nm of detection wavelength. These results are shown in Table 1. The image on FLA2000 is shown in FIG. 1.

TABLE 1

|  | Fluorescence intensity |
|---|---|
| Compound 5 | 4500 |
| Compound 6 | 5000 |
| Cy 5-dUTP | 600 |

As shown in Table 1 and FIG. 1, it was found that Compound 5 and Compound 6 each having no sulfonic acid group showed significantly higher fluorescence intensity than Cy 5-dUTP conjugate having two sulfonic acid groups. Namely, it was found that fluorescence intensity was higher in the compounds having fewer sulfonic acid group(s), indicating that the effect of reduced charges was greater than contributions of molecular weights and hydrophilic groups.

Example C-2

Preparation of Fluorescent Dye-labeled DNA Probe using Indolenine Cyanine-dUTP Conjugate cRNA was prepared by acting T7 RNA polymerase on pBlueScriptIISK(+) -α-2-HS-glycoprotein as a template (MEGAscript, Ambion). RNaseOUT (Gibco BRL) (40 U), dATP (500 µM), dGTP (500 µM), dCTP (500 µM), dTTP (200 µM), Compound 7 or Compound 8 (100 µM), SuperScript II reverse transferase (Gibco BRL) (400 U), and DEPC-treated water (up to total volume of 20 µl) were added to a mixture of cRNA and Primer 1 (SEQ ID NO. 1: TGGCCGCCTTCAACGCTCAG), and the mixture was reacted at 42° C. for 2 hours.

After completion of the reaction, the reaction was stopped and cRNA was decomposed by adding EDTA and NaOH and incubating the mixture at 65° C. for 1 hour. The reaction solution was passed through CentriSep column (PRINCETON SEPARATION, INC) to remove unreacted Compound 7 or Compound 8 for purification.

For comparison, the reverse transcription reaction was carried out in the same way as stated above by using the fluorescent nucleotide labeled with Cy 3 (Cy 3-dUTP conjugate; Amersham Pharmacia Biotech) instead of Compound 7 or Compound 8, and the obtained reaction product was purified.

After the purification, each of the reaction solution was subjected to agarose gel electrophoresis. The gel was stained with SYBR Green II (Molecular Probe), and was scanned by FLA2000 (Fuji Photo Film Co., Ltd.) at 532 nm of excitation wavelength and 580 nm of detection wavelength. These results are shown in Table 2. The imags on FLA2000 is shown in FIG. 2.

TABLE 2

|  | Fluorescence intensity |
|---|---|
| Cy3-dUTP | 2000 |
| Compound 7 | 6500 |
| Compound 8 | 7000 |

Figure 2:
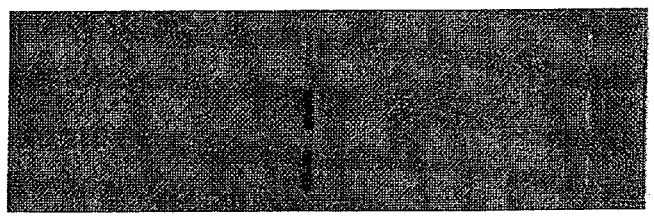
FIG. 2 shows a result of the analysis in which fluorescent dye-labeled DNA probes with indolenine cyanine-dUTP conjugates (Compound 7 and Compound 8) were subjected to agarose gel electrophoresis, and the gel was stained and scanned by FLA2000 (Fuji Photo Film Co., Ltd.) at 532 nm of excitation wavelength and 580 nm of detection wavelength after staining with SYBR Green II (Molecular Probes).

As shown in Table 2 and FIG. 2, it was found that Compound 7 and Compound 8 each having no sulfonic acid group showed significantly higher fluorescence intensity than Cy 3-dUTP conjugate having two sulfonic acid groups. Namely, it was found that fluorescence intensity was higher in the compounds having fewer sulfonic acid group(s), indicating that the effect of reduced charges was greater than contributions of molecular weights and hydrophilic groups.

The present invention provides useful fluorescent nucleotides for labeling nucleic acids, specifically, fluorescent nucleotides of which uptake ratio is high in synthetic reaction of nucleic acids.

What is claimed is:

1. A fluorescent nucleotide represented by the formula: A-B-C, wherein A represents a residue of a natural or synthetic nucleotide, oligonucleotide, or polynucleotide, and binds to B at a base moiety in said residue; B represents a divalent linking group or a single bond; and C represents a monovalent group derived from a fluorescent dye having no sulfonic acid group and no phosphoric acid group in a molecule, and having a sulfonamide group in said molecule.

2. The fluorescent nucleotide according to claim 1, wherein the fluorescent dye is a cyanine, merocyanine, or styryl fluorescent dye.

3. The fluorescent nucleotide according to claim 2, wherein the cyanine, merocyanine, or styryl fluorescent dye is a fluorescent dye having a structure represented by the following formulae,

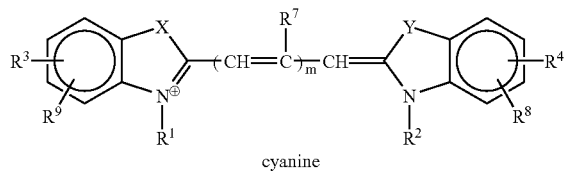

cyanine

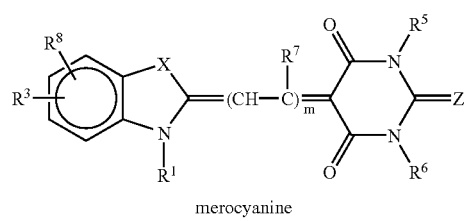

merocyanine

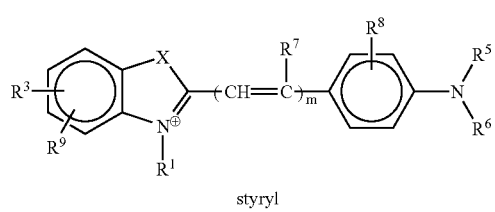

styryl

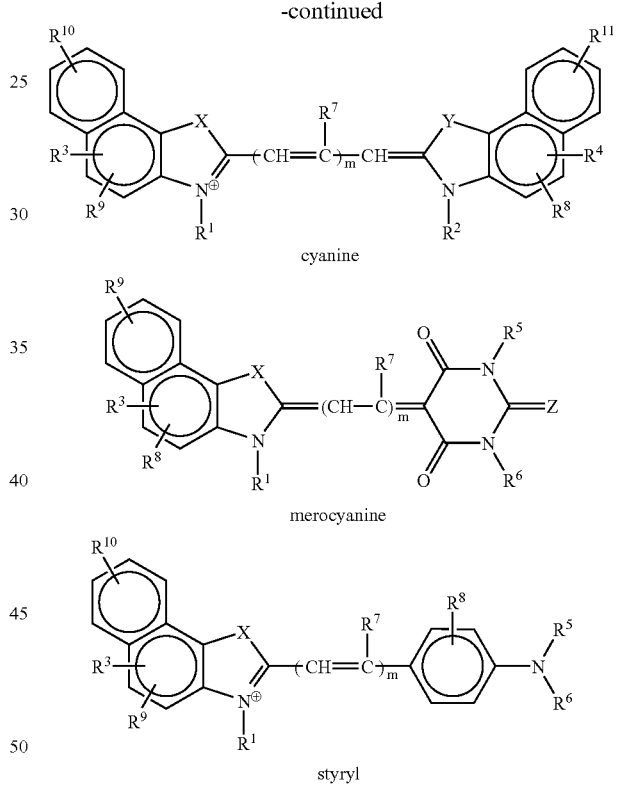

wherein X and Y are each independently selected from the group consisting of O, S, and $C(CH_3)_2$; Z is selected from the group consisting of O and S; m is an integer selected from the group consisting of 1, 2, 3 and 4; $R^1$ and $R^2$ each independently represent a hydrogen atom or an alkyl group that may be substituted with a reactive group capable of covalently binding to B, and an oxygen atom or a sulfur atom may be involved in an alkyl chain of the alkyl group, wherein at least one of $R^1$ and $R^2$ represents an alkyl group that may be substituted with a reactive group capable of covalently binding to B; and $R^3$ to $R^{11}$ each independently represent a hydrogen atom or a monovalent substituent, and two adjacent groups thereof may bind to form a ring.

4. The fluorescent nucleotide according to claim 3, wherein at least one of $R^1$ and $R^2$ is an alkyl group substituted with a carboxyl group.

5. The fluorescent nucleotide according to claim 1, wherein A is a residue of a nucleotide.

6. The fluorescent nucleotide according to claim 1, wherein A represents a residue of natural or synthetic nucleotide selected from (1) the group consisting of nucleotides consisting of AMP, ADP, ATP, GMP, GDP, GTP, CMP, CDP, CTP, UMP, UDP, UTP, TMP, TDP, TTP, 2-Me-AMP, 2-Me-ADP, 2-Me-ATP, 1-Me-GMP, 1-Me-GDP, 1-Me-GTP, 5-Me-CMP, 5-Me-CDP, 5-Nle-CTP, 5-MeO-CMP, 5-MeO-CDP, and 5-MeO-CTP; and (2) the group consisting of deoxynucleotides and dideoxynucleotides corresponding to said nucleotides.

7. The fluorescent nucleotide according to claim 1, wherein B is a linking group consisting of —$CH_2$—, —CH=CH—, —C≡C—, —CO—, —O—, —S—, —NH—, or combinations thereof, wherein a hydrogen atom on the linking group may be further substituted with a substituent.

8. The fluorescent nucleotide according to claim 7, wherein B is an aminoallyl group.

9. A diagnostic agent or a reagent for detecting nucleic acids, which consists of the fluorescent nucleotide according to claim 1.

10. The fluorescent nucleotide according to claim 2, wherein the cyanine, merocyanine, or styryl fluorescent dye is a fluorescent dye represented by the following formulae,

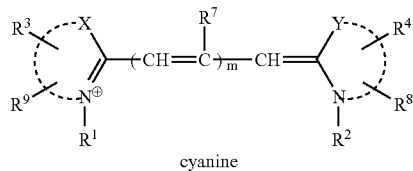

cyanine

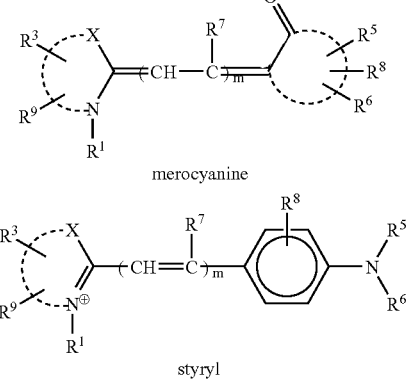

merocyanine styryl wherein X and Y are each independently selected from the group consisting of O, S, and $C(CH_3)_2$; m is an integer selected from the group consisting of 1, 2, 3 and 4; $R^1$ and $R^2$ each independently represent a hydrogen atom or an alkyl group that may be substituted with a reactive group capable of covalently binding to B, and a oxygen atom or a sulfur atom may be involved in an alkyl chain of the alkyl group, wherein at least one of $R^1$ and $R^2$ represents an alkyl group that may be substituted with a reactive group capable of covalently binding to B; $R^3$ to $R^9$ each independently represent a hydrogen atom or a monovalent substituent, and two adjacent groups thereof may bind to form a ring; and the dashed lines represent carbon atoms required to form said cyanine, merocyanine and styryl fluorescent dyes.

11. The fluorescent nucleotide according to claim 10, wherein at least one of $R^1$ and $R^2$ is an alkyl group substituted with an active ester group capable of covalently binding to an amino group, a hydroxyl group or a thiol group in the group B.

* * * * *

SEQUENCE LISTING

<160> NUMBER OF SEQ ID NOS: 1

<210> SEQ ID NO 1
<211> LENGTH: 20
<212> TYPE: DNA
<213> ORGANISM: Artificial Sequence
<220> FEATURE:
<223> OTHER INFORMATION: hypothetical sequence
<220> FEATURE:
<221> NAME/KEY: misc_feature
<222> LOCATION: (1)..(20)
<223> OTHER INFORMATION: hypothetical sequence

<400> SEQUENCE: 1
tggccgcctt caacgctcag                                          20